United States Patent
Peters et al.

(10) Patent No.: US 10,201,646 B2
(45) Date of Patent: Feb. 12, 2019

(54) DEVICE FOR REGULATING AT LEAST ONE FILTRATION VALUE, HAEMODIALYSIS MACHINE AND CORRESPONDING METHOD AND USE

(75) Inventors: Arne Peters, Bad Homburg (DE); Alexander Heide, Eppstein (DE); Christoph Wiktor, Gelnhausen (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 953 days.

(21) Appl. No.: 13/635,953

(22) PCT Filed: Mar. 17, 2011

(86) PCT No.: PCT/EP2011/001333
§ 371 (c)(1),
(2), (4) Date: Nov. 26, 2012

(87) PCT Pub. No.: WO2011/113602
PCT Pub. Date: Sep. 22, 2011

(65) Prior Publication Data
US 2013/0062283 A1 Mar. 14, 2013

(30) Foreign Application Priority Data
Mar. 19, 2010 (DE) .......... 10 2010 012 050

(51) Int. Cl.
| A61M 1/34 | (2006.01) |
| A61M 1/16 | (2006.01) |
| A61M 1/10 | (2006.01) |
| A61M 1/14 | (2006.01) |
| A61M 1/36 | (2006.01) |
| A61M 1/38 | (2006.01) |

(52) U.S. Cl.
CPC .......... *A61M 1/14* (2013.01); *A61M 1/101* (2013.01); *A61M 1/1601* (2014.02); *A61M 1/34* (2013.01); *A61M 1/3403* (2014.02); *A61M 1/36* (2013.01); *A61M 1/3607* (2014.02); *A61M 1/3693* (2013.01); *A61M 1/38* (2013.01); *A61M 1/1086* (2013.01); *A61M 2205/3375* (2013.01); *A61M 2205/3379* (2013.01); *Y10T 137/8158* (2015.04)

(58) Field of Classification Search
None
See application file for complete search history.

(56) References Cited

U.S. PATENT DOCUMENTS

| 4,113,614 A * | 9/1978 | Rollo ............. A61M 1/16 210/321.65 |
| 4,469,593 A * | 9/1984 | Ishihara .......... A61M 1/16 210/104 |
| 4,781,525 A | 11/1988 | Hubbard et al. |
| 4,964,847 A * | 10/1990 | Prince ............. G01N 33/49 436/70 |
| 6,042,784 A | 3/2000 | Wamsiedler et al. |
| 6,100,618 A | 8/2000 | Schoeb et al. |
| 6,439,845 B1 | 8/2002 | Veres |
| 6,711,943 B1 | 3/2004 | Schoeb |
| 7,131,956 B1 * | 11/2006 | Pirazzoli ........... A61M 1/16 210/645 |
| 2002/0068015 A1 * | 6/2002 | Polaschegg et al. ..... 422/44 |
| 2004/0019313 A1 * | 1/2004 | Childers et al. ....... 604/5.01 |
| 2004/0101415 A1 | 5/2004 | Schoeb |
| 2005/0131332 A1 * | 6/2005 | Kelly et al. |
| 2007/0078370 A1 * | 4/2007 | Shener ........... A61M 3/0258 604/8 |
| 2008/0312719 A1 * | 12/2008 | Keilman ......... A61N 1/37223 607/60 |
| 2009/0064755 A1 | 3/2009 | Fleischli et al. |
| 2009/0139931 A1 * | 6/2009 | Leonard .......... A61M 1/14 210/645 |
| 2009/0198170 A1 * | 8/2009 | Childers et al. |
| 2010/0036486 A1 * | 2/2010 | Mazur ........... A61M 1/1037 623/3.13 |
| 2012/0156097 A1 | 6/2012 | Beden et al. |

FOREIGN PATENT DOCUMENTS

| DE | 102 24 750 | 12/2003 |
| EP | 0 867 195 | 9/1998 |
| EP | 0 967 475 | 12/1999 |
| EP | 1 284 369 | 2/2003 |
| EP | 1 284 370 | 2/2003 |
| EP | 1 424 089 | 6/2004 |
| EP | 1 661 593 | 5/2006 |
| EP | 2 037 236 | 3/2009 |
| WO | WO 96/31934 | 10/1996 |
| WO | WO 2005/063320 | 7/2005 |
| WO | WO 2006/135934 | 12/2006 |

OTHER PUBLICATIONS

Greenwood et al. "Serial blood water estimations and in-line blood viscometry: the continuous measurement of blood volume during dialysis procedures." Clinical Science, v. 66, 1984, pp. 575-583.
Brookshier et al. "Effect of Hemotocrit on Wall Shear Rate in Oscillatory Flow: Do the Elastic Properties of Blood Play a Role?" Biorheology, 28; 1991, pp. 569-587.

* cited by examiner

Primary Examiner — Krishnan S Menon
Assistant Examiner — Bradley R Spies
(74) Attorney, Agent, or Firm — Jacobson Holman, PLLC.

(57) ABSTRACT

The present invention relates to an apparatus for the regulation of at least one filtration value in a machine for the treatment of a medical fluid, in particular in a blood treatment machine, having at least one centrifugal pumping means, to a hemodialysis machine and to a method and to a use therefor.

13 Claims, 1 Drawing Sheet

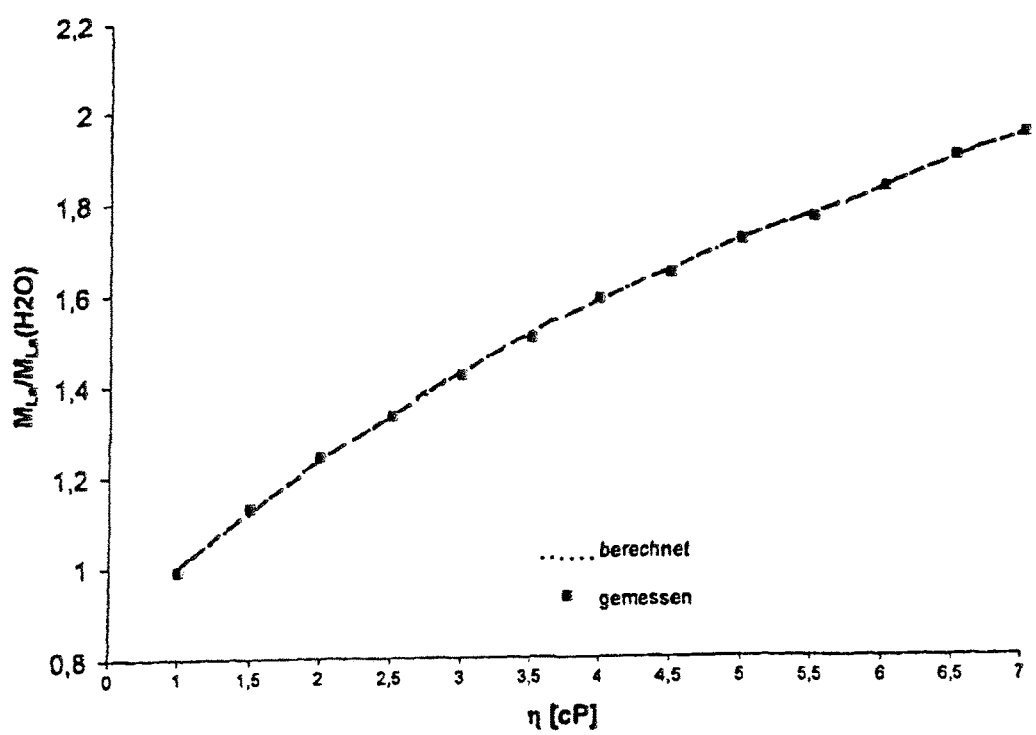

DEVICE FOR REGULATING AT LEAST ONE FILTRATION VALUE, HAEMODIALYSIS MACHINE AND CORRESPONDING METHOD AND USE

This is a national stage of PCT/EP11/001333 filed Mar. 17, 2011 and published in German, which has a priority of German no. 10 2010 012 050.2 filed Mar. 19, 2010, hereby incorporated by reference.

The present invention relates to an apparatus for the regulation of a filtration value in a machine for the treatment of a medical fluid, in particular in a blood treatment machine, as well as further in particular for use in cell separators and in apheresis, having at least one centrifugal pump means, to a hemodialyzer and to a method and a use therefor.

One of the main objects in dialysis is the removal of water from the patient's blood. Since the patient is as a rule only slightly capable, if at all, of passing water or urine, up to 3 l of water are removed from the patient during a treatment (ultrafiltration). The access to this water is only possible via the blood. If therefore there is no water in the blood, the density and viscosity of the blood increases. The blood becomes "thicker". The correlation can be explained as follows:

Blood substantially comprises plasma and blood cells. Plasma is in turn composed of water and substances dissolved therein such as electrolytes, proteins and metabolites. Red and white blood cells as well as blood platelets are spoken of with respect to blood cells, with the red blood cells being greatly predominant in number.

The hematocrit (HCT) is the portion of cellular components in the total blood volume. Due to the commonness of the red blood cells, the portion of the red blood cells in the blood volume is often used for simplification. The relative blood volume (RBV), which is used for the regulation of the ultrafiltration in the dialysis machines, is calculated from the hematocrit at the reference time ($Hct(t_0)$) and from the current hematocrit at ($Hct(t)$)

$$RBV = \frac{Hct(t_0)}{Hct(t)}$$

The density of blood plasma (~1.03 g/cm$^3$) only differs very slightly from the density of the red blood cells (~1.10 g/cm$^3$) A density spectrum of only 1.04-1.07 g/cm$^3$ thereby results with a very wide hematocrit range from 15% to 60%. The viscosity of blood, in contrast to the density, differs considerably with a varying hematocrit, as is shown in the following table:

| Hematocrit (Hct) in % | Viscosity in cP |
| --- | --- |
| 15 | 2.05 |
| 35 | 2.89 |
| 40 | 3.26 |
| 45 | 3.74 |
| 50 | 4.36 |
| 60 | 6.1 |

The increase in the density of the blood is—as described above—not particularly clear. Existing measurement processes which are intended to measure these differences in density must be able to work with corresponding precision. Since the measuring means must in any case measure from the outside through a wall of a vessel, all previous measuring methods have been greatly subject to the influences of material properties and measuring means coupling. The costs of such systems increase as the quality of the measurement path increases (e.g. exact hose diameter, cuvettes in the disposable, etc.).

Existing blood volume measurement devices can use ultrasound for the measurement of the HCT; in optical processes, a measure "light interfering particles" is determined via scattering or reflection using a light source.

It is ensured for the carrying out and monitoring of the ultrafiltration via a balancing system in accordance with EP 0 867 195 B1, for example, that the quantity of dialysate flowing into the dialyzing filter is equal to the quantity of the dialysate which flows out of the dialyzing filter again. An additional quantity of liquid can then be removed from the dialyzing filter in a controlled manner via an ultrafiltration pump. This pump generates a corresponding transmembrane pressure which removes liquid from the blood of the patient on the dialysate side via the pores of the fibers of the dialyzing filter, which is called ultrafiltration in the art. The clearance of the dialysis treatment can be increased via the addition of dilution solutions upstream (so-called predilution) or downstream (so-called postdilution) of the filter because the convective mass transport via the semipermeable membrane from the blood side to the dialysate side is further increased. Water can thus be removed from the patient in a controlled manner. A preset of the ultrafiltration rate and of an ultrafiltration target is preset by the treating physician in this respect. These known balancing systems are, however, very complex and also expensive to manufacture.

Provision is generally made in hemodialysis machines to convey the blood of the patient to be treated in the extracorporeal blood circuit by means of peristaltic pumps. Sporadically, however, using centrifugal pumps in dialysis is also described. U.S. Pat. No. 6,439,845, for example, relates to a centrifugal pump for a dialyzer which is portable and/or implantable It is furthermore also known from the prior art to use centrifugal pumps for the measurement of the viscosity of fluids, inter alia also of blood. EP 1 284 369 A1 and EP 1 284 370 A1 relate to a method and to a pump apparatus to generate an adjustable, substantially constant volume flow. In this respect, the viscosity of the fluid to be conveyed is determined in a simple manner and online by a measurement of the motor current. For this purpose, a fixed test speed of the rotor is set and the motor current at this test speed is determined for the determination of the viscosity. The viscosity of the fluid can then be determined using the known applied motor current with reference to previously carried out calibration measurements and/or calculations. The carrying out of this method is described in connection with photoresists or with suspensions of very fine solid particles in a fluid used for polishing purposes.

A method is further known from EP 2 037 236 A2 for the calibration of a throughflow measurement in a flow system as well as a flow system for the carrying out of this method. The fluid to be conveyed is conveyed through the flow system by means of a rotary pump or centrifugal pump and the throughflow quantity is determined from an electrical operating parameter of the pump and the throughflow quantity of the fluid is determined in a calibration measurement using a calibration sensor by means of ultrasound at a preset time and the throughflow measurement is recalibrated with reference to the calibration measurement.

It is further known from DE 102 24 750 A1 to provide hemodialysis machines with disposable cassette systems which can be installed in them, with these cassettes comprising substantially rigid base cassette bodies having countersunk chambers and channels and with a film covering them. In this respect, actuators and sensors are arranged in the fluid treatment machine in the installed cassette for the operation of the apparatus such that the cassettes can be used in different integration forms.

In practice, centrifugal pumps are in particular used with heart-lung machines. Such a heart-lung machine with a centrifugal pump is e.g. disclosed in EP 1 661 593 B1.

Furthermore, there was already the proposal from the prior art to utilize the viscosity of the blood as a return value for the regulation of the ultrafiltration rate in hemodialysis treatments (Greenwood, R N et al.; Serial blood water estimations and in-line blood viscometry: the continuous measurement of blood volume during dialysis procedures; in: Clinical Science, 1984, 66, pp. 575-583).

It is therefore the object of the present invention to further develop an apparatus for the treatment of a medical fluid in an advantageous manner, in particular such that it can be set up simply and simultaneously allows a very accurate determination of parameters relating to the ultrafiltration.

This object is solved in accordance with the invention by an apparatus having the features of claim 1. Provision is accordingly made that an apparatus for the regulation of at least one filtration value in a machine for the treatment of a medical fluid has at least one centrifugal pump means, wherein the viscosity of the medical fluid can be set indirectly and/or directly by means of the centrifugal pump means and wherein the at least one filtration value can be regulated with reference to the determined viscosity.

A filtration value can be a quantity to be filtered, a volume flow per time unit or another value conceivable in connection with filtration. The filtration value in this respect relates to the liquid to be treated in the machine. This liquid can be blood, for example.

The machine for the treatment of a medical fluid is in this respect a blood treatment machine in an advantageous embodiment. It is furthermore conceivable that the apparatus is used in cell separators and/or in apheresis.

The advantage thereby results that the regulation of a filtration value can take place without additional sensors being provided, for example, since the centrifugal pump means itself serves for the determination of the required regulation parameter. Expressed in simple terms, the sensor and the pump are now advantageously made at least functionally as one part. It must be pointed out in this respect that e.g. additional sensors may still be provided, e.g. for safety reasons, for the determination in particular of the flow rate; however, this is now not absolutely necessary. It is now also possible completely to dispense with cost-intensive balancing systems since a determination of the corresponding regulation parameter and a sufficiently accurate fluid conveying can be provided by the used centrifugal pump means itself. A blood volume monitor (BVM) can also be dispensed with. A significant cost reduction can hereby be achieved.

Furthermore, a substantially more accurate determination of a control variable for the determination of a filtration value is possible in comparison with the previous approaches since it is possible to focus for this purpose on the viscosity of the fluid, which provides advantages e.g. in comparison with a density measurement of the fluid. A further advantage results from the fact that a direct measurement in the fluid is now possible so that measurement errors due to indirect measurement processes do not occur.

Provision can furthermore be made that the centrifugal means is part of a centrifugal pump or is or comprises a centrifugal pump and/or that the medical fluid can be conveyed by means of the centrifugal pump means.

It is furthermore conceivable that the centrifugal pump means can be operated in at least one conveying mode and/or at least one measurement mode. Provision can be made, for example, that the centrifugal pump means runs in the conveying mode in normal operation, for instance at the preset pump rate e.g. for the extracorporeal circuit. The centrifugal pump means can then periodically be switched into a measurement mode in which the viscosity of the medical fluid can be determined indirectly and/or directly so that the at least one filtration value can be regulated with reference to the determined viscosity since a corresponding control variable is made available by the determined viscosity.

It is further conceivable that the viscosity of the medical fluid can be determined in the conveying mode of the centrifugal pump means, wherein an additional flow measurement sensor is present which determines the flow of the medical fluid. A method for this purpose is disclosed by EP 1 284 369 A1 and EP 1 284 370 A1 to which reference is made in full here.

Provision can moreover be made that the centrifugal pump means has at least one driving first part and one driven second part. It is conceivable that the parts of the centrifugal pump means, that is, the driving first part and the driven second are arranged relative to one another such that they can be pumped in the composed state, but can be separated from one another in particular after the end of the fluid treatment. This in particular facilitates the handling, but also the servicing of the centrifugal pump means.

Provision can furthermore be made that a torque and/or force transmission takes place from the driving first part to the driven second part by means of a magnetic coupling. It thereby becomes possible to enable a contactless and so low-wear torque transmission and/or force transmission.

In this embodiment, there are no losses in a mechanical support of the pumping means so that the drive torque of the pumping means is a measure for the viscosity of the pumped liquid.

It is generally conceivable that the driving first part of the centrifugal pumping means and the driven second part of the centrifugal pumping means are also coupled in a contactless manner in a different manner than by magnetic coupling.

Provision can furthermore be made that the viscosity of the medical fluid can be determined indirectly and/or directly with reference to the speed and to the driving torque of the centrifugal pumping means. This can take place, for example, with reference to the picked up motor current. It is in particular conceivable to preset a fixed engine current in the measurement mode and/or to preset a fixed speed and to determine the motor current required for it. A carrying out and evaluation can take place, for example, by means of the control and/or regulation means of the centrifugal pumping means or of the apparatus itself.

Provision can furthermore be made that the apparatus is made at least partly as a disposable or has replaceable components which are made as disposables.

It is in particular possible that at least the driven second part of the centrifugal pumping means is arranged in the disposable and/or that the disposable is made in the manner of a cassette or as a disposable cassette. This is advantageously possible since the quality of the disposable does not have any influence on the measurement parameter due to the selected measurement method.

It is furthermore also not necessary, for example, to carry out an additional coupling to the disposable. This is in particular the case when a torque transmission and/or a force transmission takes place from the driving first part to the driven second part by means of a magnetic coupling. The advantage thereby results that the necessary parameters can already be transmitted via the contactless magnetic coupling and can be determined therefrom.

It is further possible that the machine for the treatment of a medical fluid is a hemodialysis machine and/or that the filtration value or the filtration values is or are the ultrafiltration rate and/or the ultrafiltration goal. It is in particular conceivable that the ultrafiltration rate or the ultrafiltration goal can be input and/or stored into the apparatus by means of input means. The advantage thereby results that, for example, the treating physician can input these values for the ultrafiltration rate and/or the ultrafiltration goal simply in advance.

It is in particular preferred if the medical fluid is blood and that the hematocrit value of the blood can be determined with reference to the viscosity determined. The state of the blood can hereby particularly advantageously be determined. Furthermore it can be simply and advantageously determined herefrom how much fluid has already been removed from the blood so that conclusions are possible on the filtration value from this.

It is in particular also conceivable that the medical fluid is dialysate and that the state of the blood can particularly advantageously be determined with reference to the viscosity determined. It can in particular be determined simply and advantageously from this how much liquid has already been transported from the blood via the semipermeable membrane of the dialysis filter into the dialysate so that conclusions are possible on the filtration value from it. It is in particular a requirement for the regulation of the filtration that the determination of the viscosity of the medical fluid takes place downflow or downstream of the dialysis filter.

It is also conceivable that the medical fluid is filtrate, for example in the plasma separation, wherein the viscosity of the plasma filtered there can be determined in a particularly advantageous manner.

Provision can furthermore be made that the apparatus has at least one control and/or regulation means and/or has at least one connection which can be connected to at least one control and/or regulation means, wherein the viscosity of the medical fluid can be determined and/or the at least one filtration value can be regulated indirectly and/or directly by means of the control and/or regulation means.

It is furthermore conceivable that the centrifugal pumping means can be switched over between the conveying mode and the measurement mode by means of the control and/or regulation means and/or that the speed of the centrifugal pumping means can be regulated by means of the control and/or regulation means.

Provision can furthermore be made that the centrifugal pumping means has at least one closure means at the inlet side and/or at the outlet side by means of which the centrifugal pumping means can be closed at the inlet side and/or at the outlet side. Provision can in particular be made in this connection that the closure means is a clamp or a plunger which can close the inflow at the inlet side and/or at the outlet side of the centrifugal pumping means. The control of this closure means can take place, for example, by the control and/or regulation means.

It is possible that the centrifugal pumping means can be operated in the measurement mode when at least one closure means closes the centrifugal pumping means at the inlet side and/or at the outlet side, preferably when both closure means close the centrifugal pumping means at the inlet side and at the outlet side. It is conceivable to produce a complete or an almost complete recirculation via the conveying means of the centrifugal pumping means such as the rotor vane of a centrifugal pump. The viscosity of the recirculating fluid determines the speed of the rotor of the centrifugal pump at a specific driving torque of the pump. The rotor speed can in this respect be measured by known measurement devices (e.g. Hall probe, speedometer cable). The rotor speed is approximately directly proportional to the operating voltage of the centrifugal pump, so that the operating voltage can also be used as a measure for the rotor speed. The driving torque is approximately directly proportional to the operating current of the centrifugal pump so that the operating current can also be used as a measure for the driving torque. With a known rotor speed and a known driving torque of the centrifugal pump, it is possible to draw a conclusion on the viscosity of the recirculating fluid. EP 1 284 369 A1 and EP 1 284 370 A1 and also EP 0 967 475 A1 disclose methods for this purpose to which reference is made in full. Since the viscosity changes or is supposed to change during the operation of the machine for the treatment of a medical fluid, as is in particular the case in a blood treatment machine and here in particular in a hemodialysis machine, the viscosity determined thus represents information on the fluid status of the medical fluid and in particular of the blood. If the then current viscosity has been determined, a more accurate—corrected—calculation of the pump volume flow can be carried out using a new offset value of the viscosity. A particularly advantageous regulation of the at least one filtration value is thereby made possible.

It is possible in accordance with EP 0 967 475 A1, for the determination of the viscosity of the medical fluid which is conveyed by a centrifugal pumping means, to determine the viscosity from measurement parameters relating to the centrifugal pumping means or to the rotor of the centrifugal pumping means. The driving torque or the driving current of the rotor and/or the rotor speed can be measured as measurement parameters. The viscosity of the medical fluid can then be determined from the values for the driving torque or the driving current. A speed can be preset and the actual speed can be detected e.g. by means of a Hall sensor.

A further embodiment can comprise at least one detection means, in particular a flow measurement sensor, being arranged downstream or upstream of the centrifugal pumping means for the indirect and/or direct detection and/or determination of the volume flow of the medical fluid. A viscosity measurement can then take place online, that is during the conveying operation, analog to the method in accordance with EP 1 284 369 A 1 or EP 1 284 370 A1.

Provision can furthermore be made that the centrifugal pumping means can be operated in a mode with a sufficiently slow speed so that the medical fluid cannot be conveyed by the centrifugal pumping means, but can be circulated in the centrifugal pumping means or is not conveyed by the centrifugal pumping means but is circulated in it, wherein the sufficiently low speed preferably amounts to a few hundred revolutions per minute, in particular 200 r.p.m. or also lower, and wherein further preferably the viscosity of the medical fluid can be determined without additional flow measurement sensors and/or blocking apparatus. It has been found that with sufficiently low speeds of the centrifugal pumping means, for example a few hundred revolutions per minute, in particular 200 r.p.m. or also lower, no fluid is conveyed by the centrifugal pumping means, but only circulates in the centrifugal pumping means. The viscosity can then be determined in this operating mode analogously to the method presented further above without additional flow measurement sensors or blocking apparatus. In a case in which the speed is lower enough, so that e.g. no blood, dialysate or filtrate is conveyed by the centrifugal pumping means, a viscosity measurement can therefore takes place both without a clamp and without a flow measurement.

It is advantageously conceivable that the volume flow of the medical fluid is constant and/or further advantageously that the centrifugal pumping means is operated with an efficiency which is less than half the maximum efficiency, preferably with at most 20% of the maximum efficiency of the centrifugal pumping means.

The present invention furthermore relates to a hemodialysis machine having the features of claim 19. Provision is accordingly made that a hemodialysis machine has at least one apparatus in accordance with one of the claims 1 to 18.

Provision can furthermore be made that the hemodialysis machine has a mount into which a disposable can be inserted that has at least elements of the centrifugal pumping means by means of which the viscosity of the medical fluid can be determined indirectly or directly, wherein the driving first part of the centrifugal pumping means is preferably arranged in the hemodialysis machine.

The invention furthermore relates to a disposable having the features of claim 21. Provision is accordingly made that a disposable is provided for an apparatus in accordance with one of the claims 1 to 18 and/or for a hemodialysis machine in accordance with claim 19 or claim 20, wherein the disposable has at least elements of the centrifugal pumping means by means of which the viscosity of the medical fluid can be determined indirectly and/or directly, wherein the disposable preferably has the disposable features in accordance with one of the claims 7 to 18.

The invention furthermore relates to a centrifugal pumping means having the features of claim 22. Provision is accordingly made that a centrifugal pumping means is provided for an apparatus in accordance with one of the claims 1 to 18 and/or for a hemodialysis machine in accordance with claim 19 or claim 20, wherein the centrifugal pumping means has the centrifugal pumping means features in accordance with one of the claims 1 to 18.

The present invention furthermore relates to the use of an apparatus having the features of claim 23. Provision is accordingly made that an apparatus in accordance with one of the claims 1 to 18 is used for a hemodialysis machine.

The present invention furthermore relates to the use of a centrifugal pumping means having the features of claim 24. Provision is accordingly made that a centrifugal pumping means is used in a disposable, in particular in a disposable in accordance with claim 21, for an apparatus in accordance with one of the claims 1 to 18.

The present invention moreover relates to a method for the regulation of a filtration value having the features of claim 25. Provision is accordingly made that a method for the regulation of at least one filtration value in a machine for the treatment of a medical fluid, in particular in a blood treatment machine, having at least one centrifugal pumping means is carried out such that the viscosity of the medical fluid is determined indirectly and/or directly by means of the centrifugal pumping means and wherein the at least one filtration value is determined with reference to the viscosity determined.

Provision can furthermore be made that the centrifugal pumping means is operated in at least one conveying mode and/or at least one measurement mode and/or that the viscosity of the medical fluid is determined indirectly or directly with reference to the speed and driving torque of the centrifugal pumping means.

Provision can furthermore be made that the method is carried out by means of an apparatus in accordance with one of the claims 1 to 18 and/or a hemodialysis machine in accordance with either of the claim 19 or 20.

Further details and advantages of the invention will now be explained in more detail with reference to an embodiment shown in the drawing.

There is shown:

FIG. 1: the correlation between the viscosity and the hydraulic torque at a rotor speed of a centrifugal pump of 4000 r.p.m.

An embodiment of the invention by means of which a realization of the invention can take place particularly advantageously is provided in that a centrifugal pump is used instead of an occluding peristaltic hose pump for blood transport in the extracorporeal blood circuit in a hemodialysis machine. This centrifugal pump is in this respect used on the one hand in a conveying mode for the conveying of blood and on the other hand in a measurement mode for the determination of the viscosity of the blood. This value for the viscosity of the blood determined by the measurement is further used to determine the hematocrit content of the blood. In this respect, the relative blood volume can be determined with reference to the time course of the hematocrit. A control variable for the ultrafiltration is hereby generated. The apparatus in accordance with the invention is an integral element of the hemodialysis machine in this embodiment.

The ultrafiltration rate preset by the physician and the ultrafiltration target, that is, the total quantity of removed water is regulated in accordance with the invention such that no longer the absolute quantity of the fluid which is removed from the blood is monitored, but the concentration of the water in the blood via its viscosity or hematocrit content and its time course. The centrifugal pump is switched over regularly, that is, at periodically repeating intervals, from the blood conveying mode into a measurement mode for the determination of the viscosity.

The determination of the viscosity can also be determined during the conveying operation with a know fluid flow. An interruption of the fluid conveying is then no longer necessary.

For operation in the measurement mode, the pump inlets and outlets are closed for this purpose, for which purpose corresponding closure means are provided. They can, for example, be clamps or plungers which connect the inflow and outflow lines by compression. The blood in the pump chamber is then recirculated. The viscosity of the recirculating fluid determines the speed of the rotor of the centrifugal pump at a specific driving torque of the pump. The rotor speed can in this respect be measured by known measurement devices (e.g. Hall probe, speedometer cable). The rotor speed is approximately directly proportional to the operating voltage of the centrifugal pump, so that the operating voltage can also be used as a measure for the rotor speed. The driving torque is approximately directly proportional to the operating current of the centrifugal pump so that the operating current can also be used as a measure for the driving torque. With a known rotor speed and a known driving torque of the centrifugal pump, it is possible to draw a conclusion on the viscosity of the recirculating fluid. EP 1 284 369 A1 or EP 1 284 370 A1 discloses a method for this purpose to which reference is made in full. Since the viscosity changes or is supposed to change during the operation of the machine for the treatment of a medical fluid, as is in particular the case in a blood treatment machine and here in particular in a hemodialysis machine, the viscosity determined thus represents information on the fluid status of the blood. If the then current viscosity has been determined, a more accurate—corrected—calculation of the pump volume flow can be carried out using a new offset value of the viscosity. A particularly advantageous regulation of the at least one filtration value, e.g. for the ultrafiltration rate preset by the physician, and of the preset ultrafiltration goal is thereby carried out.

This comparison and the regulation based thereon is preferably carried out by the control and/or regulation means of the hemodialysis machine. For this purpose, separate control and/or regulation means can be provided in the hemodialysis machine; it is, however, equally possible that the control and/or regulation takes place by the central control and regulation unit of the hemodialysis machine.

Redundant control and/or regulation means are advantageously provided in this respect.

Additional sensors for the determination of the viscosity of the blood are not necessary when the determination of the viscosity takes place in a measurement module in which the outlets and/or inlets of the centrifugal pumping means are closed. If the determination of the viscosity takes place during the conveying of the medical fluid, at least one additional flow measurement sensor is necessary for the determination of the fluid flow.

Provision is made in a particularly advantageous embodiment that the centrifugal pump has a driving first part and a driven second part which are connected to one another in a magnetically contactless manner. The force transmission or torque transmission from the driving first part to the driven second part of the centrifugal pump thus takes place by means of a magnetic coupling. It is particularly advantageous in this connection when the driven second part of the centrifugal pumping means, that is, for example, the pump rotor of the centrifugal pump as well as the corresponding pump chamber with inflow and outflow, is an element of a disposable made in a cassette-like manner.

Such a cassette-like disposable, which can be made analog to a cassette in accordance with DE 102 24 750 A1, can be inserted into a corresponding mount of the hemodialysis machine, wherein a simple and definite insertion can be preset by corresponding connectors. In this respect, in particular the driving first part of the centrifugal pump can be arranged in the hemodialysis machine itself, and indeed in the region of the mount for the cassette. It is furthermore possible that the closure means for the inflow and the outflow of the centrifugal pump or to the centrifugal pump chamber are formed by plungers which are arranged at the machine side. These plungers can, for example, compress inflows and outflows made in channel-like form to the centrifugal pump chamber.

The details of the determination of the parameters for the regulation of the ultrafiltration will be presented theoretically in the following:

The initially introduced Table 1 shows that the viscosity changes much more noticeably at different hematocrit values than the density. In accordance with the invention, the regulation of the ultrafiltration value or the parameter for the ultrafiltration takes place with reference to the measurement of the viscosity of the blood. This measurement takes place directly in the blood and is not dependent on the quality of the disposable. A magnetically journalled disposable centrifugal pump is used for the measurement. The pump conveys the blood through the dialyzer. Occasional closing of the pump inlets and outlets results in a 100% recirculation via the rotor vane. The viscosity of the recirculating fluid determines the speed of the rotor of the centrifugal pump at a specific driving torque of the pump. The rotor speed can in this respect be measured by known measurement devices (e.g. Hall probe, speedometer cable). The rotor speed is approximately directly proportional to the operating voltage of the centrifugal pump, so that the operating voltage can also be used as a measure for the rotor speed. The driving torque is approximately directly proportional to the operating current of the centrifugal pump so that the operating current can also be used as a measure for the driving torque. With a known rotor speed and a known driving torque of the centrifugal pump, it is possible to draw a conclusion on the viscosity of the recirculating fluid. EP 1 284 369 A1 or EP 1 284 370 A1 discloses a method for this purpose to which reference is made in full. Since the viscosity changes or is supposed to change during the operation of the machine for the treatment of a medical fluid, as is in particular the case in a blood treatment machine and here in particular in a hemodialysis machine, the viscosity determined thus represents information on the fluid status of the medical fluid and in particular of the blood.

If the then current viscosity has been determined, a more accurate—corrected—calculation of the pump volume flow can be carried out using a new offset value of the viscosity.

The interconnections for the determination of the viscosity of the blood are shown again in the following:

Brookshier and Tarbell describe in Biorheology (Volume 28: p. 569-587, Pergamon Press plc., USA 1992) the dependence of the viscosity of the blood on the hematocrit: $\eta=1{,}4175+5{,}878 \cdot Hkt-15{,}98 \cdot Hkt^2+31{,}964 \cdot Hkt^3$, where HCT in %/100 and $\eta$ in cP.

The hydraulic torque $M_L$ and thus also the hydraulic power of centrifugal pump $P_L = M_L \omega$ are parameters which depend on the density $\rho$ and on the viscosity $v$ of the fluid within the pump.

In this respect there is furthermore a linear connection between the density and the volume flow. The same applies to the portion of the hydraulic torque which is independent of the volume flow and which likewise has a linear dependence on the density. There is furthermore a non-linear dependence of the portion of the hydraulic torque independent of the volume flow on the viscosity. Since the centrifugal pump is magnetically journalled and no mechanical friction losses at all hereby occur, this is mainly due to the hydraulic friction losses between the blade wheel and the housing.

On a blockage of the throughflow through the pump with any desired speed, the following relationship results for the hydraulic torque:

$$M_L(Q=0)=\rho \cdot (k_2(v) \cdot \omega^2 + k_1(v) \cdot \omega).$$

In this respect, the pump parameters k have a squared dependence on the viscosity. The pump works comparably to a rotary viscometer under these aforesaid marginal conditions.

If a fixed speed is used, it is possible considerably to reduce the calculation effort. The viscosity can then be calculated as follows:

$$\eta = k_2 M_{L0}^2 + k_1 M_{L0} + k_0.$$

This relationship is shown at a rotor speed of 4000 r.p.m. in the FIGURE.

The torque can be determined via the current pick-up of the centrifugal pump. If this parameter is known, the viscosity can be obtained and the hematocrit can be determined from it. With the hematocrit, the relative blood volume is in turn calculated and one thus has the return parameter for the regulation of the ultrafiltration.

It must also be pointed out at this point that the brief closing of both pump sides does not result in any damage to the blood.

The invention claimed is:

1. A method for the regulation of at least one blood filtration value in a machine cooperating with a disposable cassette for the treatment of blood in an extracorporeal blood circuit having at least one centrifugal blood pump, characterized in that the centrifugal blood pump has a driving part located in the machine and a driven part located in the disposable cassette and coupled with the driving part in a contactless manner, wherein the machine comprises a control device for regulating speed of the centrifugal blood pump, and characterized in that the viscosity of the blood is determined indirectly and/or directly by speed and driving torque of the centrifugal blood pump downstream of a blood filter, hematocrit of the blood is determined based solely on the viscosity determined, and with the at least one blood filtration value being regulated directly or indirectly by the control device with reference solely to the hematocrit determined based on viscosity.

2. A method in accordance with claim 1, characterized in that the centrifugal blood pump is operated in at least one conveying mode and/or at least one measurement mode.

3. A method for regulating filtration of blood in a machine cooperating with a disposable cassette in an extracorporeal blood circuit comprising the steps of
   determining viscosity of the blood indirectly or directly based on speed and driving torque of a centrifugal blood pump downstream of a blood filter, the centrifugal blood pump having a driving part located in the machine and a driven part located in the disposable cassette and coupled with the driving part in a contactless manner, wherein the machine comprises a control device for regulating speed of the centrifugal blood pump,
   determining hematocrit of the blood based solely on the determined viscosity, and
   regulating directly or indirectly by the control device at least one blood filtration value based solely on the determined hematocrit based on viscosity.

4. The method of claim 3, wherein the centrifugal blood pump is operated in at least one of a conveying mode, a measurement mode, multiple conveying modes, and multiple measurement modes.

5. The method of claim 3, wherein the driving part transmits torque by a magnetic coupling to the driven part.

6. The method of claim 3, wherein the machine for the treatment of blood is a hemodialysis machine, and wherein the at least one filtration value is at least one of ultrafiltration rate and ultrafiltration goal.

7. The method of claim 3, wherein the blood filtration value is blood volume flow.

8. The method of claim 3, wherein the centrifugal blood pump has an inlet and an outlet, at least one of the inlet and the outlet capable of closing.

9. The method of claim 8, wherein the centrifugal blood pump operates in a measurement mode when at least one of the inlet and outlet is closed.

10. The method of claim 8, wherein the filtration value is volume flow of the blood determined by at least one flow measurement sensor arranged downstream or upstream of the centrifugal blood pump.

11. The method of claim 8, wherein the viscosity is determined by circulating the blood in the centrifugal blood pump at a speed of 200 r.p.m. or less.

12. The method of claim 3, wherein the machine is a hemodialysis machine.

13. The method of claim 12, wherein the hemodialysis machine has a mount holding the disposable cassette.

* * * * *